United States Patent [19]

Forbes et al.

[11] Patent Number: 4,573,982

[45] Date of Patent: Mar. 4, 1986

[54] EYE FRAME OPHTHALMIC DRUG DELIVERY DEVICE

[75] Inventors: Alexander E. Forbes; John L. Haslam, both of Lawrence, Kans.

[73] Assignee: Merck & Co., Inc., Rahway, N.J.

[21] Appl. No.: 550,427

[22] Filed: Nov. 10, 1983

[51] Int. Cl.⁴ ........................................... A61M 35/00
[52] U.S. Cl. .................................................... 604/300
[58] Field of Search ....................... 604/174, 294-300; 351/158

[56] References Cited

U.S. PATENT DOCUMENTS 3,209,755 10/1965 McCarthy et al. ................. 604/174
3,446,209 5/1969 Macha ................................. 604/295
3,934,585 6/1976 Maurice ............................... 604/298
4,183,355 1/1980 Meckler .............................. 604/295

OTHER PUBLICATIONS

F. Gorgahn (Derwent Abstract G6772W/26).

Primary Examiner—Dalton L. Truluck
Attorney, Agent, or Firm—Manfred Polk; Michael C. Sudol, Jr.; Mario A. Monaco

[57] ABSTRACT

This invention relates to an eyeglass frame mounted unit dose ophthalmic drug delivery device. A unit dose of ophthalmic medicament is provided by either a preloaded disposable microsyringe, preloaded disposable tip or manually loaded calibrated microsyringe rigidly mounted on a block which itself is slidably mounted to the eyeglass frame. The device allows for the insertion of ophthalmic medication into the inferior cul de sac of the eye.

6 Claims, 6 Drawing Figures

EYE FRAME OPHTHALMIC DRUG DELIVERY DEVICE

BACKGROUND OF THE INVENTION

In general, administration of ophthalmic medicaments and drug solutions to the eye has been difficult to accomplish and is generally inefficient. The most commonly employed way to administer said medicaments to the eye is to administer drops to the eye by means of an eye dropper or squeeze bottle. When this form of administration is used, the patient is required to tilt his or her head back or to lie down. This method is both messy and wasteful due to misalignment, patient blinking, inaccurate dosage and muscle control problems in many adults.

BACKGROUND OF THE INVENTION

In general, administration of ophthalmic medicaments and drug solutions to the eye has been difficult to accomplish and is generally inefficient. The most commonly employed way to administer said medicaments to the eye is to administer drops to the eye by means of an eye dropper or squeeze bottle. When this form of administration is used, the patient is required to tilt his or her head back or to lie down. This method is both messy and wasteful due to misalignment, patient blinking, inaccurate dosage and muscle control problems in many adults.

Review of prior art has shown that F. Gorbahn (Derwent Abstract G6772W/26) developed an eye glass frame with a stationary mounting plate for the eye dropper. The device patented by A. Macha (U.S. Pat. No. 3,446,209) April, 1966, is very similar to Gorbahn's but could also use a squeeze bottle applicator. In January, 1980, M. Meckler (U.S. Pat. No. 4,183,355) improved on this method. He employed an eye glass frame mounted set of slides for positioning the eye dropper directly over a reclining patient's eyes. Alignment was improved. All of these devices, however, did not address the major problems of inaccurate dosage, wasteful and messy delivery.

The particular eye glass frame mounted unit dose ophthalmic drug delivery device of this invention does innovatively address and overcome these problems and consistently delivers an exact unit dosage of ophthalmic medicament or drug to the inferior cul de sac of the eye.

SUMMARY OF THE INVENTION

The advantages of our ophthalmic drug delivery device herein described are several.

(1) The patient uses a unit dose medication that has been preloaded for exact dosage and there is no spilling of contents or inaccurate dose measurments as in the old systems whereby the drops could have run out of the eye or not even gotten into the eye.

(2) The eyeglass frame mounted unit dose ophthalmic drug delivery device of our invention is universally adjustable so that after the initial setting the patient does not need to readjust the frames.

(3) The patient's head remains erect and the ophthalmic medication or drug solution is delivered directly into the inferior cul-de-sac of the eye thus eliminating any problems of said drug or solution running out of the eye.

(4) Many older patients who lack muscle control will be able to use this device effectively since once it is adjusted to the patients physical feature it is rather easy to administer the ophthalmic drug or medication to the eye.

Thus it is an object of this invention to provide an ophthalmic drug delivery system which will deliver a unit dosage to the inferior cul-de-sac of the dye. It is a further object of this invention to provide a ophthalmic drug delivery device, that is universally adjustable to fit all patients and that once an initial setting is made no further adjustments are needed or warranted. It is a further object of this invention to provide a device wherein the patients head is in an erect position while the dose is administered to the inferior cul-de-sac of the eye and to provide a patient with a great deal more flexibility than is known in the prior devices and particularly in self-dosing and in cutting down of wasted medication.

DETAILED DESCRIPTION OF THE INVENTION

Figure 1:
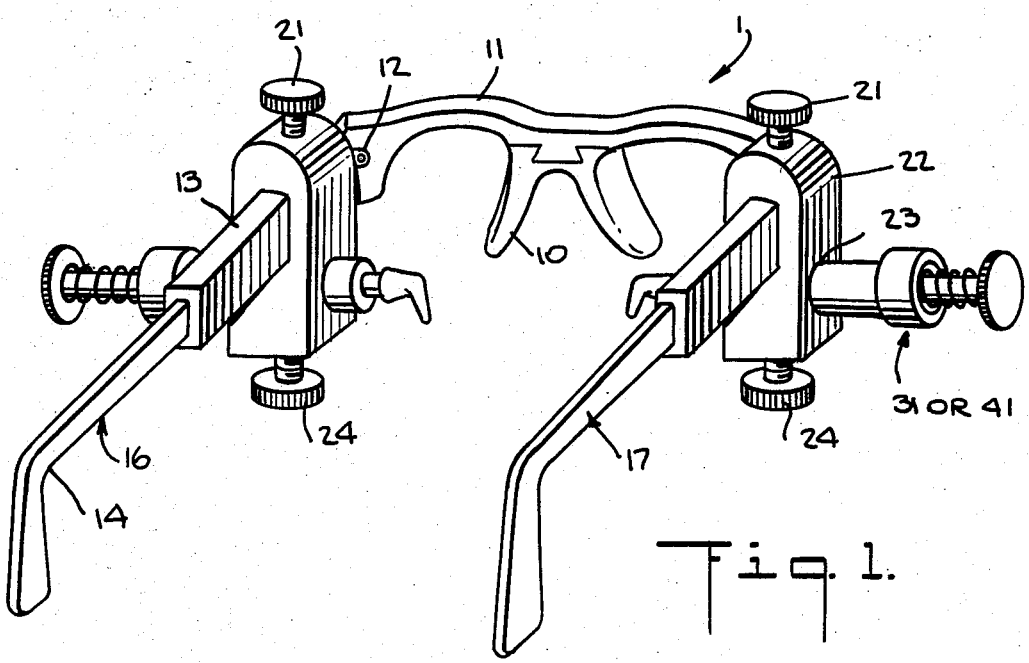
Figure 2:
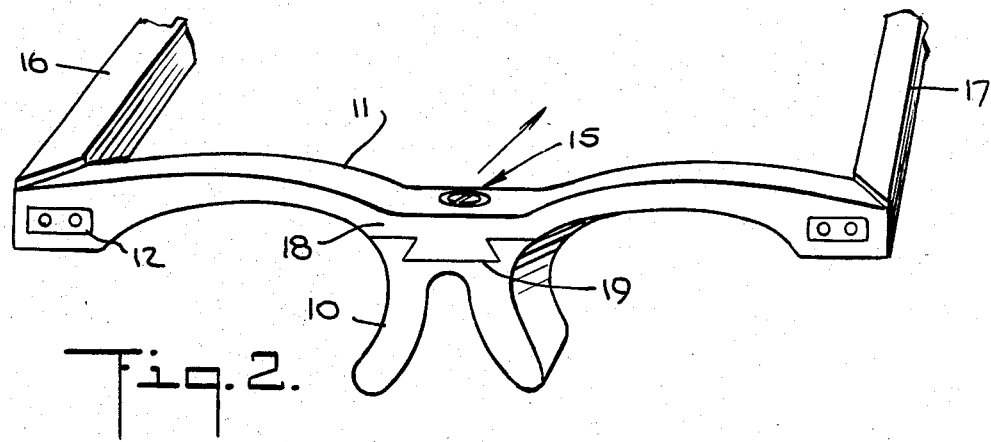
Figure 3:
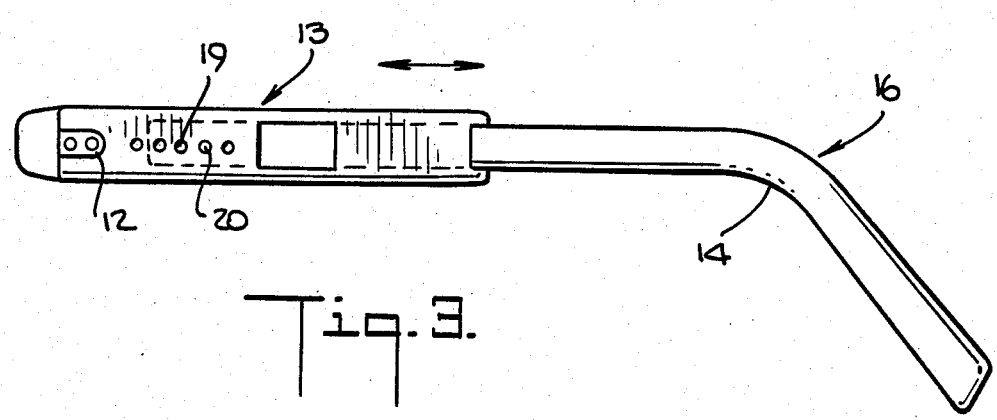
Figure 4:
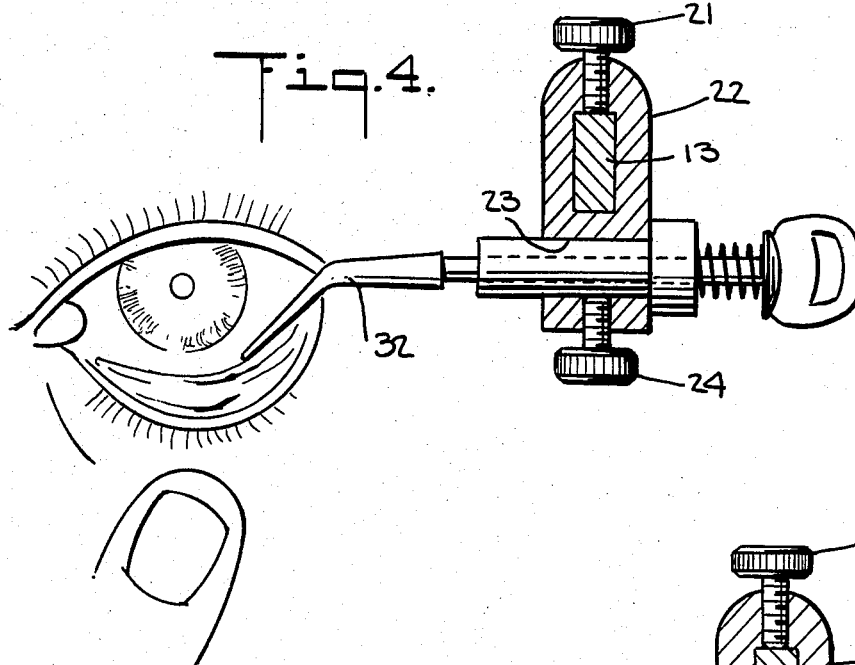
Figure 5:
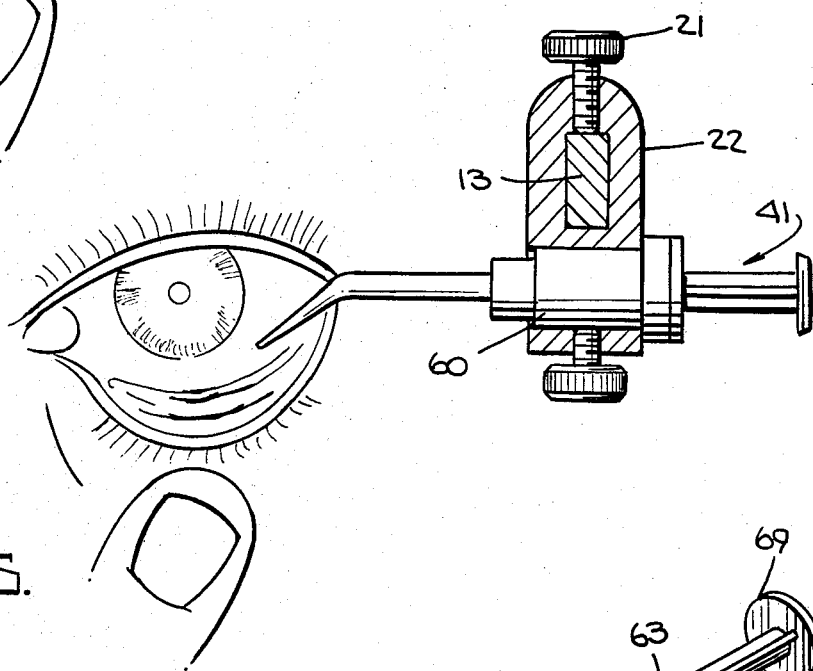
Figure 6:
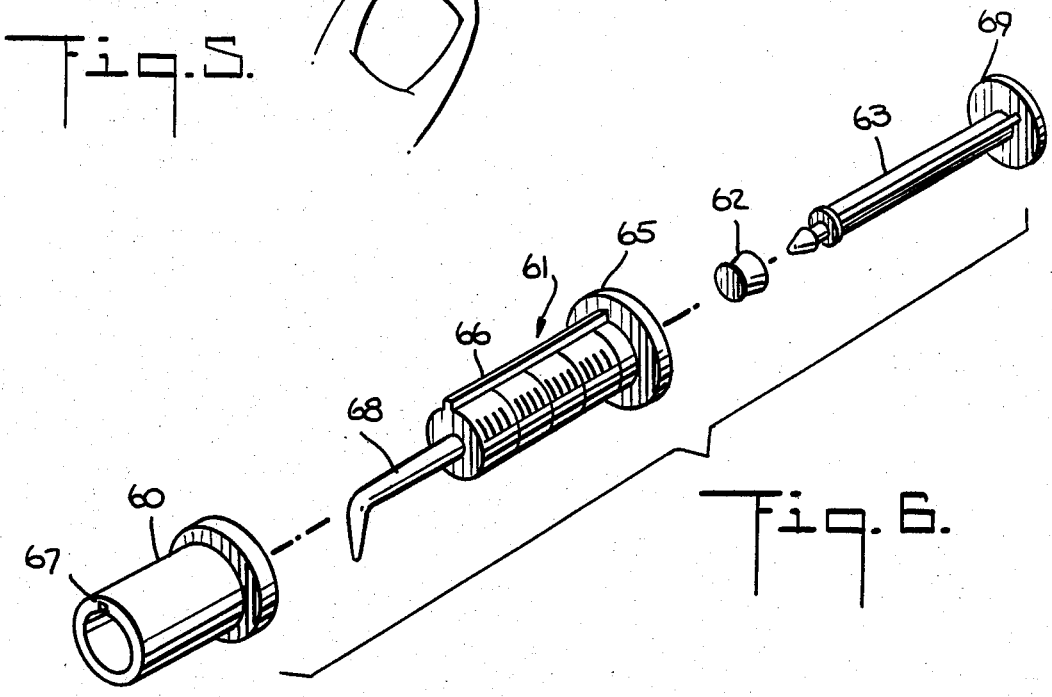

To provide a better understanding of this invention there are provided six figures showing the various embodiments of the invention. FIG. 1 is an isometric view illustrating the assembly of the complete ophthalmic drug delivery device. FIG. 2 is a detailed illustration of the adjustable bridge feature with repositionable nose pads of this device. FIG. 3 is a detailed drawing of the adjustable temple of the drug delivery device. FIG. 4 illustrates the disposable unit dose tip installed on a microsyringe which is part of this device and FIG. 5 illustrates the positioning of the disposable microsyringe while FIG. 6 illustrates in detail the disposable syringe.

Referring now to the figures, particularly FIG. 1, there is shown a frame mounted unit dose ophthalmic drug delivery device 1. The eyeglass-like framed drug delivery device is made up of two basic pieces, namely the bridge portion 11 and two temples 16 and 17. The two temple pieces, 16 and 17, are hinged by means of hinges 12 to each end of the bridge piece 11 to form a typical eyeglass frame. Slidably mounted on each temple is a block 22 on which a microsyringe 31 or 41 is adjustably mounted to each block.

Referring now in detail to each particular part of the eyeglass frame drug delivery device, there is shown in FIG. 2 a detailed front view of the bridge portion of the eyeglass bridge 11. On the bridge 11 is shown a built in adjustable nose pads 10 mounted on the lower part of the bridge 11 at about its central area. The nose pads 10 fit on the nose of the patient and allow said frames to rest comfortably and in a specific position when being used by the patient to administer medicament to the eyes. The nose pads 10 are adjustably mounted on the bridge 11 by means of a male and female dovetail joint. At the center lower part of the bridge there is constructed a male dovetail joint 18 whereas the nose pads are constructed having a female dovetail 19. These dovetails are so constructed that the nose pads 10 can be slidably adjusted along the bridge 11. The adjustment of the nose pads in relation to the bridge is provided by a set screw 15 used to lock the nose pads to the bridge once the patient has properly positioned the nose pads. Adjustment of the nose pads compensates for the individual differences in depth which each patient's eyes are set into the skull. At each end of the bridge 11 the temple portions of the drug delivery device 16 and 17 are mounted by means of hinge assemblies 12.

FIGS. 1 and 3 show particular detail of the temple portions 16 and 17 of the drug delivery device. To allow the temple pieces to be adjustable to fit the device comfortably on the patients ears, each temple piece 16 and 17 is composed of a channel temple 13 which has a series of holes 19 whose center line corresponds to nibs 20 located on the sliding ear lobe portion 14 of the temple pieces 16 and 17. This telescoping sliding and locking action provides the mechanism of adjustment for the temples. When a person needs to adjust the temples he merely pulls out or pushes in the sliding ear lobe portion 14 of the temples such that the nibs 20 move along and are aligned with the various holes 19 on the channel portion of the temple piece 13.

As shown in FIGS. 1, 4 and 5 the channel portion of the temple 13 acts as a support for the syringe block 22. Thus the syringe blocks 22 are made with a hole therein of a shape slightly larger than the rectangular shape of a cross section of the channel temple portion 13 such that the block 22 can slide along the channel temple portion 13. The block 22 serves a double purpose in that it acts as a rigid holder for the syringe 31 or 41 and secondly it securely attaches the syringe assembly to the channel temple 13.

In order to adjust the blocks 22 in a position convenient to administer the medicament or drug solution to the patient's eye there are provided thumb screws 21 on the top portion of the block 22. To adjust the block along the temple portion 13 one merely opens the thumb screw 21 moves the block to the desired position and tightens the thumb screw 21. Tightening the thumb screw against the temple portion 13 rigidly sets the block in the desired position.

As a final portion to the eye glass frame drug delivery device FIGS. 1, 4, 5 and 6 show the syringe 31 or 41 slidably mounted in the block 22. The syringe portions 31 or 41 are slidably mounted in the block 22 through a hole 23 in said block, 22. The axis of the hole 23 in said block 22 is perpendicular to the logitudinal axis of the temple pieces 13. The barrel of the syringe is of a diameter such that it can be slidably adjusted through the hole 23. A set screw 24 similar to the set screw 21 rigidly fixes the adjustment of the syringe 31 or 41. Thus, if the syringe must be moved inward toward the patients eye one merely opens the set screws 24, adjust the syringe and tightens the set screw 24.

The drug delivery device herein described can generally employ two types of syringes for controlling drug delivery. First a unit dose microsyringe 31 employs a disposable sterile tip 32 as shown in FIG. 4. This tip can be either preloaded with the unit dose or the microsyringe which is calibrated can be manually loaded with the unit dose. A disposable tip and mating microsyringe are designed so that there is only one possible alignment after mounting.

A second type of unit disposable microsyringe 41 is completely presterilized and preloaded with a unit dose. This type of syringe is shown part 60 in FIGS. 5 and 6.

As shown in FIGS. 5 and 6 this second type unit disposable syringe consists of a flanged cylindrical portion 60 which rests in hole 23 in block 22 and is adjusted by set screw 24. Fitting into the body of the cylindrical portion 60 is the main syringe barrel 61. Syringe barrel 61 has on one end a flange 65 which prevents the barrel from passing through the cylindrical portion 60 and in fact forms a stop with flanged cylindrical portion 60. Barrel 61 can also have a guide 66 mounted along its length which guide moves in a depression 67 in the cylindrical portion 60 to keep the syringe and particularly the drop portion 68 on proper alignment with the patient's eye. Piston 63 with end portion 62 and outer flanged portion 64 forms the final part of the syringe. Thus to administer a unit dose of ophthalmic drug one merely pushes the piston until its outer flange portion 69 stops against flange 65. The unit dose drops out of the drop portion 68 into the patient's eye.

In order to use the device of this invention one must make four adjustments before the drug solution can be administered to the eye. These include: one, adjusting the nose pads 10 so that the eye glass frame is comfortably resting on the patients nose, secondly, adjusting the position of the block 22 on the temple piece 13, thirdly, adjusting the syringe 31 or 41 along the block 22 so that the tip 32 or 68 is just above the cul-de-sac of the eye when the frame is in the final position on the patient and fourth adjusting the length of the slidable temple piece 14 so that the eye glass frame comfortably fits on the patients face being comfortable around the ears and on the nose. These adjustments do not have to be performed in the order above given but can be varied according to the preferences of the patient. Once the preferred orientation of the ophthalmic drug delivery device to the eye is reached no further adjustments will be necessary. The syringe is then used to administer the medicament or drug to the inferior cul-de-sac by the patient pulling the lower eyelid down and outside the conforming cavity to receive the medicament or drug solution liquid whereupon the plunger of the syringe is expressed expelling the contents. Once the drug has been injected into the inferior cul-de-sac the lower eyelid is released with little to no waste of the dosage.

The ophthalmic medicaments and drug solutions which can be used in the drug delivery device of this invention can be any ophthalmic medicament or drug solution which the patient needs to administer eye drops for any ailment of the eyes. Thus for example if the patient has glaucoma he can administer ophthalmic drug medicament useful for glaucoma such as timolol, propine and the like. Anyone skilled in the art would realize that any type ophthalmic drug or medicament can be administered in this manner comfortably and once the position of the drug delivery device has been set medically no reset of any of the adjustments on the eye glass frame drug delivery device of this invention is further required.

All the parts of the drug delivery device, namely the bridge, temples, and block can be constructed of lightweight material, particularly any type plastic material commonly used for the preparation of eyeglass frames. Also, metals can be used although this would increase the cost of any drug delivery device. Typically, the nose pads can be made of material which would rest comfortably on the patients nose and the end of the temples of the patients ear can be coated with material to make the eye glass frames rest comfortably on the patients ears. The syringes 31 and 41 which are used as parts of the device are typical syringes which are commonly available. There is no inventive feature in the syringe itself.

The above is a description of the invention and should be considered an illustration of the invention and not be considered a limitation thereof. Obvious embodiments of the invention are intended to be included herein.

What is claimed is:

1. A universally adjustable ophthalmic drug delivery device comprising: (a) a bridge having an adjustable nose piece thereon; (b) temples hingedly mounted at the ends of the bridge piece for securing said device to a patient's ears; (c) a pair of blocks slidably mounted on the channel portion of said temples; (d) a pair of syringes slidably mounted, perpendicular to the longitudinal axis of said temples, on said blocks said syringe ends terminating in the vicinity of the patient's eye such that the block and syringe are so adjusted to fit and deliver a dose of ophthalmic medicament to the lower cul-de-sac of the patient's eye.

2. The drug delivery device of claim 1 wherein the temples are adjustable to conform to the patients face characteristics.

3. The drug delivery device of claim 1 wherein the temples are comprised of a slidably mounted temple piece and a channel temple into which the slidable temple fits.

4. The drug delivery device of claim 1 wherein the syringe is a throw away type.

5. The drug delivery device of claim 1 wherein the syringe is slidably adjusted within the block and contains a disposable tip.

6. The drug delivery device of claim 1 wherein the block and syringe are adjustable through the use of set screws.

* * * * *